United States Patent
Verkade et al.

(10) Patent No.: US 8,436,057 B1
(45) Date of Patent: May 7, 2013

(54) ANION EXCHANGE MEMBRANE

(75) Inventors: John G. Verkade, Ames, IA (US);
Kuldeep Wadhwa, Sugar Land, TX (US); Xueqian Kong, Ames, IA (US); Klaus Schmidt-Rohr, Ames, IA (US)

(73) Assignee: U.S. Department of Energy, Washington, DC (US)

( * ) Notice: Subject to any disclaimer, the term of this patent is extended or adjusted under 35 U.S.C. 154(b) by 515 days.

(21) Appl. No.: 12/706,877

(22) Filed: Feb. 17, 2010

(51) Int. Cl.
*C07F 9/54* (2006.01)

(52) U.S. Cl.
USPC ............ 521/30; 521/25; 521/32; 568/11; 568/728

(58) Field of Classification Search ............ 521/30, 521/25, 32; 568/11, 728
See application file for complete search history.

(56) References Cited

U.S. PATENT DOCUMENTS

| | | | | |
|---|---|---|---|---|
| 4,303,551 A | * | 12/1981 | Vaughan | 502/159 |
| 5,051,533 A | * | 9/1991 | Verkade | 564/13 |
| 6,017,969 A | * | 1/2000 | Jones et al. | 521/32 |
| 2005/0070615 A1 | * | 3/2005 | Terajima et al. | 521/25 |
| 2008/0051480 A1 | * | 2/2008 | Terajima et al. | 521/30 |

FOREIGN PATENT DOCUMENTS

| | | | |
|---|---|---|---|
| JP | 07-289924 | * | 11/1995 |
| JP | 07-289924 | * | 11/1996 |

* cited by examiner

*Primary Examiner* — Peter D. Mulcahy
*Assistant Examiner* — Henry Hu
(74) *Attorney, Agent, or Firm* — Brian J. Lally; Michael J. Dobbs; John T. Lucas

(57) ABSTRACT

An anion exchange membrane and fuel cell incorporating the anion exchange membrane are detailed in which proazaphosphatrane and azaphosphatrane cations are covalently bonded to a sulfonated fluoropolymer support along with anionic counterions. A positive charge is dispersed in the aforementioned cations which are buried in the support to reduce the cation-anion interactions and increase the mobility of hydroxide ions, for example, across the membrane. The anion exchange membrane has the ability to operate at high temperatures and in highly alkaline environments with high conductivity and low resistance.

30 Claims, 2 Drawing Sheets

ANION EXCHANGE MEMBRANE

GOVERNMENT INTERESTS

The United States Government has rights in this invention pursuant to Contract No. DE-AC02-07CH11358, between the U.S. Department of Energy (DOE) and Iowa State University, representing The Ames Laboratory.

FIELD OF THE INVENTION

One or more embodiments of the present invention relates to an anion exchange membrane. In addition, one or more embodiments of the present invention relate to use of an anion exchange membrane in a fuel cell. Another embodiment of the present invention relates to a process for preparing an anion exchange membrane.

BACKGROUND

Interest in fuel cells as a means of generating electricity for use in various systems has increased significantly in recent years. Generally, a fuel cell comprises two electrically conductive electrodes, an anode and cathode, which are separated from each other by an ion-conducting membrane, or electrolyte. Fuel cells use electrons that are separated from a fuel and transported through an external circuit as electricity. A number of fuel cells exist that use a variety of fuels, electrolytes, and materials for the cathode and anode, among other variables.

Hydrogen-fueled proton-exchange membrane fuel cells (PEMFCs) have been thoroughly researched and developed and provide good performance and power densities that are obtainable with low catalyst loadings. In operation of a PEMFC, hydrogen is split into protons and electrons on the anode side of the cell, with the protons permeating through a proton exchange membrane, such as Nafion®, to the cathode, while the electrons are forced through an external circuit, thus generating electricity, to the cathode. At the cathode of a PEMFC, oxygen is supplied and reacts with the hydrogen that has traveled through the polymer electrolyte membrane and the electrons that have traveled through the external circuit to form water. However, PEMFCs have little tolerance for carbon monoxide and, thus, their operation is limited when hydrogen is supplied from the steam reformation of light hydrocarbons, which is currently the primary source of hydrogen as a fuel. In addition, PEMFCs utilize expensive, precious-metal catalysts at the anode and cathode, thus making their commercialization not feasible.

Alkaline fuel cells (AFCs) are another well developed category of fuel cell technologies that have been extensively used in NASA's space shuttle program. An AFC produces electricity as a result of a redox reaction between hydrogen and oxygen. Hydrogen is oxidized at the anode producing water and electrons, while oxygen is reduced at the cathode after the electrons generated at the anode pass through an external circuit. The anode and cathode are separated by a porous matrix saturated with an aqueous alkaline solution, such as potassium hydroxide (KOH). The advantages of AFCs include the ability to operate at lower catalyst loadings and utilize a broader range of catalysts, including the less expensive metals nickel and silver. However, the use of methanol as a fuel is not suitable with the use of AFCs containing a liquid alkaline electrolyte because of the formation of carbonate that results from conversion of KOH to $K_2CO_3$ in the presence of $CO_2$. The formation of the metal carbonate precipitate can block and destroy the electrode and catalyst layers.

Recently, considerable interest has also been shown in solid polymer membrane direct methanol fuel cells (DMFCs) due to the high energy density and reversible efficiencies of methanol (energy density, $W_e$=6.1 kWh/kg; reversible efficiency, $\eta_{rev}$=0.97) compared with liquid hydrogen ($W_e$=2.6 kWh/kg; $\eta_{rev}$=0.83). In addition, DMFCs operate at moderate temperatures and the replacement of a methanol fuel cartridge is relatively simple. There are two methods through which a DMFC may operate—proton-transport and anion-transport. In a DMFC with proton-transport, i.e., utilizing a proton exchange membrane, the reactions through an acid membrane are as follows:

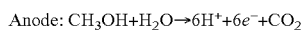
Anode: $CH_3OH+H_2O \rightarrow 6H^++6e^-+CO_2$

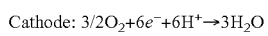
Cathode: $3/2O_2+6e^-+6H^+ \rightarrow 3H_2O$

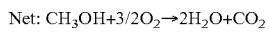
Net: $CH_3OH+3/2O_2 \rightarrow 2H_2O+CO_2$

However, the use of proton exchange membranes in DMFCs present significant disadvantages, namely: (1) parasitic crossover of methanol from the anode to the cathode which leads to a lowering of cell voltage and efficiency; (2) electroosmosis of water from the anode to the cathode, which causes flooding at the cathode; and (3) reduced catalytic kinetics in the acidic environment requiring high loadings of expensive precious-metal catalysts, e.g., platinum.

As a result, various approaches to increase DMFC performance are currently being investigated, including the use of solid alkaline anion-exchange membranes (AAEMs), as opposed to the aqueous alkaline solution found in AFCs. The use of AAEMs with a direct methanol fuel source is advantageous because it combines the positive aspects of PEMs (all solid construction), AFCs (favorable electrokinetics) and DMFCs (high energy density of methanol), while also being able to minimize the disadvantages of each, including operating in the presence of carbonate species.

A fuel cell utilizing an AAEM for the direct use of methanol as a fuel has the same net reaction as using a proton exchange membrane, but undergoes the following reactions at the anode and cathode:

Anode: $CH_3OH+6OH^- \rightarrow CO_2+5H_2O+6e^-$

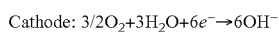
Cathode: $3/2O_2+3H_2O+6e^- \rightarrow 6OH^-$

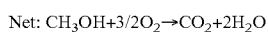
Net: $CH_3OH+3/2O_2 \rightarrow CO_2+2H_2O$

Multiple efforts have been made to obtain functional AAEMs that optimize the potential advantages discussed above. Information relevant to attempts to address these problems can be found in U.S. Pat. No. 6,183,914, issued to Yao, et al., and, U.S. patent application Ser. No. 11/630,994 (Publn. No. 2008/0124604), filed Jun. 1, 2005, which are incorporated by reference herein. Additional efforts are described in Danks, T. N., et al., *J. Mater. Chem.* 2002, 12, 3371-3373; Danks, T. N., et al., *J. Mater. Chem.*, 2003, 13, 712; J. R. Varcoe, et al., *Chem. Mater.*, 2007, 19, 2686-2693; J. R. Varcoe, et al., *Chem. Mater.*, 2007, 19, 2686-2693; J-S. Park, et al., *J. Power Sources* 2008, 178, 620-626, all of which are also incorporated by reference herein. However, each one of these references suffers from one or more of the following disadvantages: low radiation resistance, mechanical instability or degradation at elevated temperatures, and/or instability or degradation at elevated alkaline concentrations.

For example, poly(vinylidene fluoride) (PVDF) and poly (tetrafluoroethern-co-hexafluoropropylene) (FEP) have been grafted with 4-vinylbenzyl chloride, followed by modification of the benzyl chloride functionality with trimethylamine to give the trimethylbenzylammonium salt. Danks, T. N., et al., *J. Mater. Chem.* 2002, 12, 3371-3373. The PVDF-based AAEM degraded on subsequent amination and conversion to the alkaline form for hydroxide ion exchange. Danks, T. N., et al., *J. Mater. Chem.*, 2003, 13, 712. The FEP-based AAEM gave conductivities of 0.02 S/cm at ambient temperatures and humidity of 100%, but was still brittle and contained tears. J. R. Varcoe, et al., *Chem. Mater.*, 2007, 19, 2686-2693.

As noted above, these efforts have not yielded an anion exchange membrane that is stable and able to operate with reduced resistance and high conductivity at elevated operating temperatures or in highly alkaline environments typically found in a direct methanol fuel cell. In addition, the prior membranes incorporate quaternary ammonium salts as the ionophore, which experience intense cation-anion interaction with the hydroxide ions crossing the membrane, thus impeding hydroxide mobility and lowering the conductive capacity of the membrane. Finally, the prior efforts often involve complex steps for synthesis of the membrane, such as radiation grafting.

SUMMARY

One or more embodiments of the present invention relate to an anion exchange membrane which comprises a sulfonated fluoropolymer support covalently bonded to the phosphorus atom of one or more bicyclic proazaphosphatrane cations.

In another embodiment of the present invention, the anion exchange membrane comprises a sulfonated fluoropolymer support covalently bonded to one of the equatorial nitrogen atoms of one or more tricyclic azaphosphatrane cations.

In another embodiment, the anion exchange membrane of the present invention comprises groups of bicyclic proazaphosphatrane and/or tricyclic azaphosphatrane cations covalently bonded to a sulfonated fluoropolymer support.

Other embodiments of the present invention provide for a fuel cell having an anion exchange membrane comprising a sulfonated fluoropolymer support covalently bonded to groups of bicyclic proazaphosphatrane and/or tricyclic azaphosphatrane cations. In another embodiment, the present invention provides for a fuel cell having an anion exchange membrane described above interposed between an anode and cathode.

One of the multiple embodiments of the present invention also provides a method for preparing an anion exchange membrane, as described above, comprising the steps of: (a) immersing a sulfonated fluoropolymer support in a solution of phosphatrane salt and organic solvent; (b) reacting the solution and support of step (a) in order to bond the phosphatrane ion to the sulfonyl group of the sulfonated fluoropolymer support, wherein the polarity of the sulfonated fluoropolymer support is inverted in order to facilitate anion exchange across the membrane. Additional embodiments of the present invention include: (c) removing any unreacted phosphatrane salt from the support solution; and, (d) soaking the support in hydroxide solution.

One feature of one or more embodiments of the present invention is found in the sulfonated fluoropolymer support. Such a support provides strong mechanical and thermal stability that can withstand the high temperatures and stress present in a fuel cell. In addition, the sulfonated fluoropolymer support maintains excellent electrical conductivity due to the combination of the hydrophobic polymer backbone and flexible hydrophilic functional side groups.

Another salient aspect of the one or more embodiments of the present invention is the inversion of the polarity of the sulfonated fluoropolymer support through the addition of bicyclic proazaphosphatrane and/or tricyclic azaphosphatrane cations. This modification of the sulfonated fluoropolymer support imparts previously absent characteristics that allow for its present use as an anion exchange membrane in highly alkaline environments.

Another feature of one or more embodiments of the present invention is the presence of various phosphatrane cations covalently bonded to the sulfonyl groups of the sulfonated fluoropolymer support. The cage-like structure of the phosphatrane cation provides stability and increases performance in strongly basic conditions by minimizing cation-anion interactions thereby increasing hydroxide mobility across the membrane due to the various resonance structures that reduce the charge density. The cage-like structure of the phosphatrane cation also makes the cation compact, protecting the carbon and phosphorous atoms from nucleophilic attack and subsequent ring opening reactions.

BRIEF DESCRIPTION OF THE DRAWINGS

These and other features, aspects, and advantages of the multiple embodiments of the present invention will become better understood with reference to the following description, appended claims, and accompanied drawings where:

DETAILED DESCRIPTION

Figure 1:
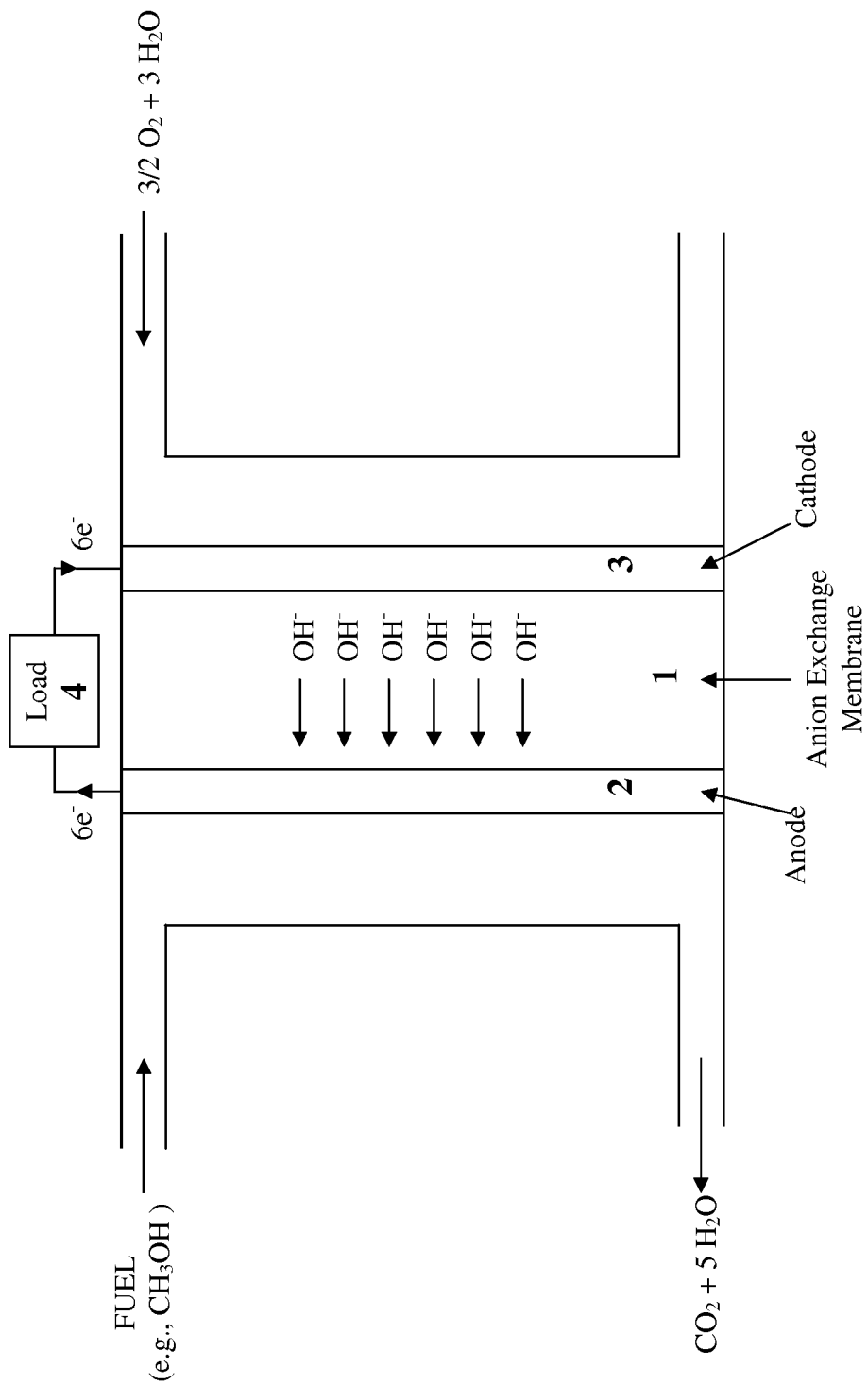
FIG. 1 is a schematic representation of a fuel cell incorporating one embodiment of the anion exchange membrane of the present invention.

Generally, the present invention is directed to an anion exchange membrane comprising a sulfonated fluoropolymer support to which a phosphatrane cation is covalently bonded. The attachment of the cation inverts the polarity of the starting sulfonated fluoropolymer support to enable anion transportation, which was not possible with the starting sulfonated fluoropolymer support. The surprising and unexpected stability and conducting capability of the resulting anion exchange membrane in basic conditions, which are also expected at elevated temperatures, is an important feature of one or more embodiments of the present invention.

As used herein, the term "sulfonated" means a compound having one or more sulfonic acid functional groups having the formula $SO_3M$, [wherein M is hydrogen (thereby providing an acid), or an alkali metal salt or an alkaline earth metal salt (thereby providing a sulfonated salt)], $SO_2F$ or $SO_2Cl$. Preferred sulfonic acid functional groups are $SO_2F$ and $SO_3H$. The term "sulfonyl group" as used herein means an organic radical or functional group having the general formula $R—SO_2—R^1$ obtained from a sulfonic acid functional group through the removal of two hydroxyl groups or other relevant groups. As it relates to the present invention, R is a fluoropolymer or copolymer and $R^1$ is preferably $OH^-$ or F.

As used herein, the term "fluoropolymer support" generally means a fluorocarbon based polymer. "Fluoropolymer support," as used herein, includes multiple types of fluorocarbons, including perfluorinated, partially fluorinated and fully fluorinated supports, as well as fluorocarbon derivatives such as polytrifluorochloroethylene (PTFCE). In addition, "fluoropolymer support" is not limited to a singular fluorocarbon based polymer, but may comprise multiple fluorocarbon polymers and/or derivatives in the same support. "Fluoropolymer support" is further defined as described in the examples below.

As used herein, the term "phosphatrane" refers to proazaphosphatrane and azaphosphatrane, unless specifically designated as one or the other by express language or reference to a structure representing one or the other. The term "proazaphosphatrane" means a bicyclic, nonionic base. Proazaphosphatranes are a chemical precursor to azaphosphatranes which are formed when the phosphorus atom becomes protonated. The term "azaphosphatrane" refers to a tricyclic proazaphosphatrane in which the phosphorus atom is protonated and in which a transannular bond forms between the bridgehead phosphorus and basal nitrogen atom.

As used herein, "individually" means that the R groups can be the same or different.

I. Sulfonated Fluoropolymer Support

Various sulfonated fluoropolymer supports which are known in the art can be used in accordance with the present invention. Unmodified sulfonated fluoropolymer membranes are often used in proton exchange membranes (PEM) in which the membrane transports $H^+$ ions from the anode to the cathode.

For example, known sulfonated fluoropolymer supports compatible with the present invention include but are not limited to those described in U.S. Pat. No. 3,282,875, issued to Connolly, et al.; U.S. Pat. No. 3,985,501, issued to Grot; U.S. Pat. No. 7,455,934, issued to Araki, et al.; Ivanchev, *Russian Journal of Applied Chemistry* (2008), vol. 81, no. 4, pp. 569-584, which are incorporated by reference herein. One of the most commonly used PEMs is a sulfonated fluoropolymer known as Nafion®, which is a sulfonated tetrafluoroethylene based polymer.

In addition, methods for preparing a sulfonated fluoropolymer, such as adding a sulfonic acid functional group to a fluoropolymer, are well known in the art. Examples of such methods include but are not limited to the copolymerization of tetrafluoroethylene and a derivative of perfluoro(alkyl vinyl ether) with sulfonyl acid fluoride and grafting styrene on to Teflon® and subsequently sulfonating the aromatic rings. Mauritz, K. A., Moore, R. B., *Chem. Reviews* (2004) 104, 4535-4585, and Qiu, J., et al., *Radiation Physics and Chem.* (2007) 76, 1703-1707. Examples of well known fluoropolymers include but are not limited to polytetrafluoroethylene (PTFE, or Teflon®), perfluoroalkoxy polymer resin (PFA), fluorinated ethylene-propylene (FEP), polyethylene-tetrafluoroethylene (ETFE, Tefzel® or Fluon®), polyvinylfluoride (PVF, or Tedlar®), polyethylene-chlorotrifluoroethylene (ECTFE, or) Halar®, polyvinylidene fluoride (PVDF, Kynar®, Solef® or Hylar®), and polychlorotrifluoroethylene (PCTFE). Sulfonic acid functional groups may be bonded to a fluoropolymer by any number of methods known in the art.

Examples of preferred sulfonated fluoropolymer supports in connection with one or more embodiments of the present invention are supports of the Nafion® variety.

While sulfonated fluoropolymer supports, and methods of preparing such supports, are known for use as proton conductors in proton exchange membranes, the one or more embodiments of the present invention described in detail below focus on inverting the polarity of those supports through the addition of groups of Formula (I) and/or (II) to support anion exchange, which is not possible with a sulfonated fluoropolymer support. In essence, the one or more embodiments of the present membranes are the exact opposite of presently used sulfonated fluoropolymer supports. Through this modification, an anion conducting membrane, in contrast to a proton conducting membrane, is formed that is surprisingly conductive and stable in basic conditions and at high temperatures for extended periods of time.

II. Prozaphosphatrane Cation

One embodiment of an anion exchange membrane of the present invention comprises a sulfonated fluoropolymer support and groups of bicyclic proazaphosphatrane cations wherein one or more proazaphosphatrane cations are covalently bonded at the phosphorous atom to one or more sulfonyl groups of the sulfonated fluoropolymer support.

One embodiment of an anion exchange membrane of the present invention comprises a sulfonated fluoropolymer support, as described above, and groups of formula (I)

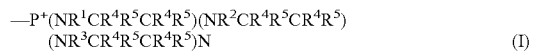
—P$^+$(NR$^1$CR$^4$R$^5$CR$^4$R$^5$)(NR$^2$CR$^4$R$^5$CR$^4$R$^5$)
(NR$^3$CR$^4$R$^5$CR$^4$R$^5$)N        (I)

covalently bonded to a sulfonyl group of the fluoropolymer support, wherein $R^1$, $R^2$ and $R^3$ are independently H, a $C_{1-5}$ alkyl group, a benzyl group, $C_{5-9}$ aryl group, $C_{1-4}$alkyl$C_{6-9}$aryl, $((C_{1-4})alkyl)_3Si$, $CH(Me)Ph$, $Si(CH_3)_3$, or 2,2-dimethylpropyl;

wherein $R^4$ and $R^5$ are independently H, a $C_{1-5}$ alkyl group, a $C_{5-9}$ aryl group, or a benzyl group; and, wherein a positive charge resides at the phosphorus atom or at any of the three equatorial nitrogen atoms bonded to the phosphorus atom.

A proazaphosphatrane cation used in the scope of the one or more embodiments of the present invention, and written as Formula I above, is a bicyclic phosphatrane cation. The attachment of this cation completes the polarity inversion of the sulfonated fluoropolymer support that is integral to the one or more embodiments of the present invention. This process has not had great success in previous research.

In one or more embodiments, the phosphorus atom of one or more proazaphosphatrane cations is covalently bonded to one or more sulfonyl groups of the sulfonated fluoropolymer support. As described in more detail below, the distribution of the positive charge over the proazaphosphatrane cation in its various resonance structures inhibit anion-cation interactions thereby increasing anion mobility across the anion exchange membrane. In addition, the cage-like structure depicted below is quite unstrained and, therefore, very stable. The cage-like structure also makes the phosphatrane cation compact, which protects the phosphorus and carbon atoms from nucleophilic attack and consequent ring opening reactions. In addition, the P—S bond in an anion exchange membrane utilizing a proazaphosphatrane cation is known to be strong. All of these attributes contribute to the stability of the one or more embodiments and their ability to effectively operate in harsh and strongly basic conditions at elevated temperatures.

Proazaphosphatranes of Formula (I) typically possess the following structure:

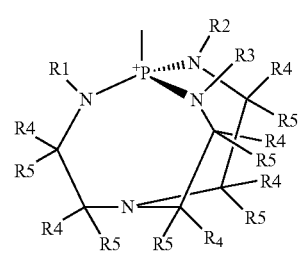

The groups of Formula (I) have a number of resonance structures in which the positive charge is distributed on different atoms, thus reducing the charge density of the molecule. For example, the positive charge may reside on any of four heteroatoms (three equatorial nitrogen atoms and one phosphorus atom), as exhibited in the following resonance structures:

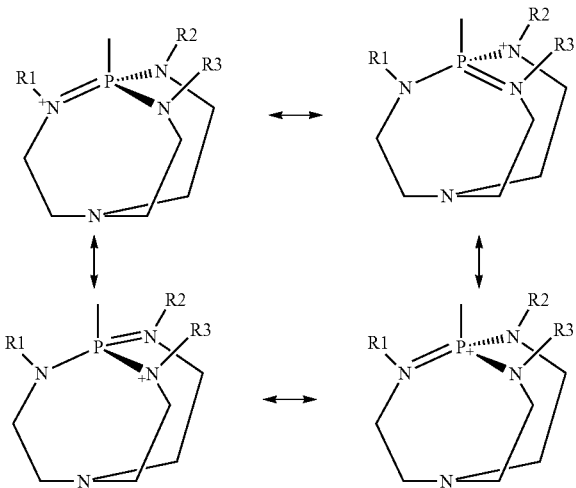

The structural characterization of one or more embodiments of the present invention is described in further detail in X. Kong, et al., *Macromolecules,* 2009, 42, 1659-1664, which is incorporated herein by reference. The distribution of the positive charge provides a low positive charge density for a relatively large cation, which limits the possibility that the positive charge will impede the mobility of the negatively charged hydroxide ions.

As described above, proazaphosphatranes of Formula I having a variety of groups attached to the nitrogen and carbon atoms are compatible with the multiple embodiments of the present invention. In one of the multiple embodiments of the present invention, $R^1$, $R^2$, $R^3$, $R^4$ and $R^5$ are H in Formula I.

In another embodiment, $R^1$, $R^2$ and $R^3$ of Formula I are methyl groups, while $R^4$ and $R^5$ are H.

In another embodiment, $R^1$ is H, $R^2$ and $R^3$ of Formula I are methyl groups, while $R^4$ and $R^5$ are H.

In another embodiment, $R^1$ is H, $R^2$ and $R^3$ of Formula I are methyl groups, while $R^4$ and $R^5$ are independently H or a propyl group.

In another embodiment, $R^1$, $R^2$ and $R^3$ of Formula I are independently H or a methyl group, while $R^4$ and $R^5$ are independently H or a benzyl group.

In another embodiment, $R^1$, $R^2$ and $R^3$ of Formula I are independently H or a methyl group, while $R^4$ and $R^5$ are H.

In another embodiment, $R^1$ is H, $R^2$ and $R^3$ are ethyl groups, and $R^4$ and $R^5$ are H.

In another embodiment, $R^1$ is H, $R^2$ and $R^3$ are propyl groups, and $R^4$ and $R^5$ are H.

In another embodiment, $R^1$ is H, $R^2$ and $R^3$ are butyl groups, and $R^4$ and $R^5$ are H.

In another embodiment, $R^1$, $R^2$ and $R^3$ of Formula I are independently H or a methyl group, while $R^4$ and $R^5$ independently are a $C_{1-5}$ alkyl group.

In yet another embodiment, $R^1$, $R^2$ and $R^3$ of Formula I are benzyl groups, while $R^4$ and $R^5$ are H.

In another embodiment, $R^1$, $R^2$ and $R^3$ of Formula I are independently H or a propyl group, while $R^4$ and $R^5$ are H.

In another embodiment, $R^1$, $R^2$ and $R^3$ of Formula I are CH(Me)Ph, while $R^4$ and $R^5$ are H.

In another embodiment, $R^1$, $R^2$ and $R^3$ of Formula I are $Si(CH_3)_3$, while $R^4$ and $R^5$ are H.

In another embodiment, $R^1$, $R^2$ and $R^3$ of Formula I independently are H or a $C_{1-5}$ alkyl, while $R^4$ and $R^5$ independently are $C_{1-5}$ alkyl groups.

In another embodiment, $R^1$, $R^2$, $R^3$, $R^4$ and $R^5$ of Formula I independently are H or a $C_{1-5}$ alkyl groups.

In another embodiment, $R^1$, $R^2$ and $R^3$ of Formula I are 2,2-dimethylpropyl, while $R^4$ and $R^5$ are H.

In another embodiment, $R^4$ and $R^5$ are independently $C_{1-5}$ alkyl groups.

In another embodiment, at least one of $R^1$, $R^2$, $R^3$, $R^4$ and $R^5$ of Formula I is H.

In another embodiment, at least two of $R^1$, $R^2$, $R^3$, $R^4$ and $R^5$ of Formula I is H.

In another embodiment, at least three of $R^1$, $R^2$, $R^3$, $R^4$ and $R^5$ of Formula I is H.

In another embodiment, at least one of $R^1$, $R^2$, $R^3$, $R^4$ and $R^5$ of Formula I is $CH_3$.

In another embodiment, at least two of $R^1$, $R^2$, $R^3$, $R^4$ and $R^5$ of Formula I is $CH_3$.

In another embodiment, at least three of $R^1$, $R^2$, $R^3$, $R^4$ and $R^5$ of Formula I is $CH_3$.

It is believed that crowding the equatorial nitrogen atoms with groups other than H, e.g., alkyl groups or aryl groups, will provide some selectivity in synthesizing an anion exchange membrane having primarily groups of Formula I covalently bonded to the sulfonyl groups of the fluoropolymer support. In such a case, the starting phosphatrane used to synthesize such a membrane would include alkyl groups, or larger groups, on each $R^1$, $R^2$ and $R^3$. The size of the $R^4$ and $R^5$ groups would be unlikely to negatively affect the stability or conductivity efficiency of the membrane, but may increase the difficulty of synthesis.

Thus, an additional embodiment where $R^1$ is H, $R^2$ and $R^3$ are $CH_3$, and $R^4$ and $R^5$ are independently $C_{1-5}$ alkyl groups will increase selectivity for anion exchange membranes possessing groups of Formula I in which there is a strong P—S bond present.

Proazaphosphatranes are bicyclic, non-nucleophilic, strong non-ionic bases that can become protonated on their phosphorus atom, instead of their nitrogen atoms, to form azaphosphatranes with a transannular bond between the basal nitrogen atom and phosphorus atom. With respect to one or more embodiments of the present invention, proazaphosphatrane refers to a compound that forms a covalent bond between one or more sulfonyl groups of the fluoropolymer support and the phosphorus atom of one or more proazaphosphatrane cations when bonded to a sulfonated fluoropolymer support a covalent bond without forming a transannular bond.

Since the initial synthesis of proazaphosphatranes by one of the present inventors [U.S. Pat. No. 5,051,533, issued to J. G. Verkade, incorporated by reference herein], several such compounds have become commercially available from Aldrich Chemical, Strem Chemicals and Digital Specialties. A phosphatranium salt formed from the protonation of a proazaphosphatrane with an acid is also available from Aldrich. In the synthesis of this phosphatrane compound, the intermediate phosphatranium cation chloride is obtained by converting tris(2-ethylamino)amine ("tren") into the corresponding mono-, di-, or trialkylated tetramine, which is then reacted with $ClP(NMe_2)_2$. Subsequent deprotonation of the cation with KO-t-Bu yields the corresponding proazaphosphatrane.

Further details on the synthesis of various phosphatrane-related compounds compatible with one or more embodiments of the present invention, including proazaphosphatranes and azaphosphatranes, are described in U.S. Pat. No.

5,051,533; Laramay, M. A. H., Verkade, J. G., *Z. anorg. allg. Chem.*, 1991, 605, 163-174; Kisanga, P. B., J. G. Verkade, *Tetrahedron*, 2001, 57, 467-475; Verkade, J. G., *Top. Curr. Chem.*, 2003, 223, 1; Verkade, J. G., Kisanga, P. B., *Tetrahedron*, 2003, 59, 7819-7858; Verkade, J. G., Kisanga, P. B., *Aldrichimica Acta*, 2004, 37, 3-14; D'Sa, Bosco A., Verkade, John G., *Phosphorous, Sulfur and Silicon and the Related Elements* (Gordon & Breach Science Publishers), 1997, 123, 301-312, which are incorporated by reference herein.

For example, an unsymmetrical phosphatrane having one H group and two R groups on the equatorial nitrogen atoms can be produced as follows: monobenzyl tren (PhCH$_2$NHCH$_2$CH$_2$)N(CH$_2$CH$_2$NH$_2$)$_2$) is synthesized by controlling the stoichiometric ratio of benzaldehyde to tren to make the intermediate (PhCH$_2$NH=CHCH$_2$)N (CH$_2$CH$_2$NH$_2$)$_2$), followed by hydrogenation to (PhCH$_2$NHCH$_2$CH$_2$)N(CH$_2$CH$_2$NH$_2$)$_2$). This two-step sequence is referred to as reductive amination. Subsequently, the other two amine groups are alkylated analogously (simultaneously or stepwise) via reductive amination with a suitable R group (which can be the same or different) to yield PhCH$_2$NHCH$_2$CH$_2$N(CH$_2$CH$_2$NHR)$_2$. The benzyl group is then deprotected using palladium/hydrogen to yield NH$_2$CH$_2$CH$_2$N(CH$_2$CH$_2$NHR)$_2$, followed by closing the cage with ClP(NMe$_2$)$_2$ to obtain the desired phosphatrane salt using the known procedure as for other phosphatrane salts. See Thomas, E. W., et al., J. Medicinal Chem. (1992), 35 (7), 1233-1245 (for preparation of benzyl-protected [(cyclododecyl)NHCH$_2$CH$_2$]$_2$NCH$_2$CH$_2$NHCH$_2$Ph and (NH$_2$CH$_2$CH$_2$)$_2$NCH$_2$CH$_2$NHCH$_2$Ph); Baxter, E. W., Reitz, A. B., Organic Reactions (2002) 59 (preparation of (NH$_2$CH$_2$CH$_2$)$_2$NCH$_2$CH$_2$NHCH$_2$Ph)); and, D'Sa, B. A., Verkade, J. G., Phosphorous, Sulfur and Silicon and the Related Elements (1997), 123, 301-312 (synthesis of H$_2$NCHCH$_2$N(CH$_2$CH$_2$N-i-Pr)$_2$).

A variety of phosphatrane salts may also be obtained using carbon-substituted tren analogues that are subsequently reacted with ClP(NMe$_2$)$_2$. For example, the following tren analogues having various R groups have been synthesized: (HRNCHRCH$_2$)$_3$N, namely, chiral (HR'NCHRCH$_2$)$_3$N(R=i-Pr; R'=Me) and chiral (H$_2$NC*HRCH$_2$)$_3$N(R=i-Pr) (Pei, Y., et al., *European J. Org. Chem.*, 2005, 13, 2835-2840); chiral (R*NHCH$_2$CH$_2$)$_3$N (namely, (S,S,S)-PhHMeCNHCH$_2$CH$_2$)$_3$N) (Liu, X., et al., *J. Organ. Chem.*, 2000, 65, 701-706); and chiral (R'NHC*HRCH$_2$)$_3$N (namely, (S,S,S)—CH$_3$NH(CH$_2$Ph)CH$_2$)$_3$N) (You, J. S., et al., *Tetrahedron*, 2004, 60, 7877-7883). Other carbon substituted tren analogues may be similarly synthesized by standard organic synthesis approaches known in the art.

III. Azaphosphatrane Cation

Another embodiment presents an anion exchange membrane having groups of bicyclic proazaphosphatrane cations and tricyclic azaphosphatrane cations attached to one or more sulfonyl groups of the sulfonated fluoropolymer support at the phosphorus atom.

In another embodiment of the present invention, the anion exchange membrane includes, in addition to groups of Formula I, azaphosphatranes of Formula II:

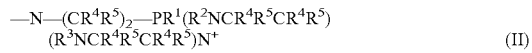

covalently bonded to one or more sulfonyl groups of the fluoropolymer support, wherein R$^1$ is H, a C$_{1-5}$ alkyl group, a benzyl group or a halogen;

wherein R$^2$ and R$^3$ are independently H, a C$_{1-5}$ alkyl group, a benzyl group, a C$_{5-9}$ aryl group, a C$_{1-4}$alkylC$_{5-9}$aryl, ((C$_{1-4}$)alkyl)$_3$Si, CH(Me)Ph, Si(CH$_3$)$_3$, or 2,2-dimethylpropyl;

wherein at least one of R$^1$, R$^2$ and R$^3$ is H;

wherein R$^4$ and R$^5$ are independently H, a C$_{1-5}$ alkyl group, a C$_{5-8}$ aryl group, or a benzyl group; and, wherein a positive charge resides at the basal nitrogen atom.

Alternatively, the anion exchange membrane may contain only groups of Formula II as further described herein.

An azaphosphatrane cation used in the scope of the one or more embodiments of the present invention, and written as Formula II above, is a tricyclic phosphatrane cation. The attachment of this cation completes the polarity inversion of the sulfonated fluoropolymer support that is integral to the one or more embodiments of the present invention. The azaphosphatrane cation is formed when the phosphorus atom becomes protonated, thereby forming a transannular bond between the phosphorus atom and positively charged basal nitrogen atom. In one or more embodiments of the present invention, any one of the three equatorial nitrogen atoms of the one or more azaphosphatrane cations is covalently bonded to one or more sulfonyl groups of the sulfonated fluoropolymer support. Azaphosphatranes also possess a cage-like structure that is quite compact and unstrained, thereby contributing the membrane's ability to effectively operate in harsh and strongly basic conditions at elevated temperatures for an extended period of time.

Azaphosphatranes of Formula II typically possess the following tricyclic structure:

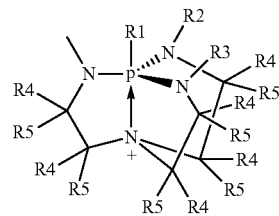

Groups of Formula II are similar to groups of Formula I, with a few notable exceptions. First, in Formula II, the sulfonyl group of the fluoropolymer support is bonded to an equatorial nitrogen atom of the phosphatrane compound, as opposed to the phosphorus atom of Formula I. In addition, as described above, groups of Formula II have a transannular bond between the phosphorus atom and basal nitrogen atom. Finally, the basal nitrogen atom is positively charged in groups of Formula II, which represents a fifth resonance structure in addition to the four analogous structures depicted for proazaphosphatrane above. The distribution of the positive charge over the entire cage further assists in facilitating the transport of hydroxide ions across the anion exchange membrane.

As described above, azaphosphatranes of Formula II having a variety of groups attached to the phosphorus, nitrogen and carbon atoms are compatible with the multiple embodiments of the present invention. In one of the multiple embodiments of the present invention, R$^1$, R$^2$, R$^3$, R$^4$ and R$^5$ are H in Formula II.

In another embodiment, at least one of R$^1$, R$^2$ and R$^3$ is H and the other groups are independently C$_{1-4}$ alkyl groups, while R$^4$ and R$^5$ independently are unbranched C$_{1-5}$ alkyl groups.

In another embodiment, at least one of $R^1$ and $R^2$ are independently $C_{1-5}$ alkyl groups, $R^3$ is H and $R^4$ and $R^5$ independently are unbranched $C_{1-5}$ alkyl groups.

In another embodiment, $R^1$ is a methyl group, $R^2$, $R^3$, $R^4$ and $R^5$ are H.

In another embodiment, $R^1$ is a methyl group, $R^2$ is H, $R^3$ is a $C_{1-5}$ alkyl group, and $R^4$ and $R^5$ are H.

In another embodiment, $R^1$ is a methyl group, $R^2$ is H, $R^3$ is a methyl group, and $R^4$ and $R^5$ are H.

In another embodiment, $R^1$ is a methyl group, $R^2$ is H, and $R^3$, $R^4$ and $R^5$ are methyl groups.

In another embodiment, $R^1$ is a methyl group, $R^2$ is H, $R^3$ is a propyl group, and $R^4$ and $R^5$ are H.

In another embodiment, $R^1$ is an ethyl group, and $R^2$, $R^3$, $R^4$ and $R^5$ are H.

In another embodiment, $R^1$ is a propyl group, and $R^2$, $R^3$, $R^4$ and $R^5$ are H.

In another embodiment, $R^1$ is a butyl group, and $R^2$, $R^3$, $R^4$ and $R^5$ are H.

In another embodiment, $R^1$ is a benzyl group, and $R^2$, $R^3$, $R^4$ and $R^5$ are H.

In another embodiment, $R^1$ is a benzyl group, $R^2$ is H, $R^3$ is a methyl group, and $R^4$ and $R^5$ are H.

In another embodiment, $R^1$ is a benzyl group, $R^2$ is H, $R^3$ is a methyl group, and $R^4$ and $R^5$ are H.

In another embodiment, $R^1$ is fluorine or chlorine, and $R^2$, $R^3$, $R^4$ and $R^5$ are H.

In yet another embodiment, $R^1$ is fluorine, $R^2$ is H, $R^3$ is a methyl group, and $R^4$ and $R^5$ are H.

In another embodiment, $R^1$ is fluorine, $R^2$ is H, $R^3$ is a benzyl group, and $R^4$ and $R^5$ are H.

In another embodiment, $R^1$ is chlorine, and $R^2$, $R^3$, $R^4$ and $R^5$ are H.

In another embodiment, $R^1$ is H, $R^2$ and $R^3$ are independently a $C_{1-5}$ alkyl or halide group, and $R^4$ and $R^5$ are H.

In another embodiment, $R^1$ is a $C_5$ aryl group, and $R^2$, $R^3$, $R^4$ and $R^5$ are H.

In another embodiment, $R^1$ is a $C_5$ aryl group, $R^2$ is H, $R^3$ is a methyl group, and $R^4$ and $R^5$ are H.

In another embodiment, at least one of $R^1$, $R^2$, $R^3$, $R^4$ and $R^5$ of Formula I is H.

In another embodiment, at least two of $R^1$, $R^2$, $R^3$, $R^4$ and $R^5$ of Formula I is H.

In another embodiment, at least three of $R^1$, $R^2$, $R^3$, $R^4$ and $R^5$ of Formula I is H.

In another embodiment, at least one of $R^1$, $R^2$, $R^3$, $R^4$ and $R^5$ of Formula I is $CH_3$.

In another embodiment, at least two of $R^1$, $R^2$, $R^3$, $R^4$ and $R^5$ of Formula I is $CH_3$.

In another embodiment, at least three of $R^1$, $R^2$, $R^3$, $R^4$ and $R^5$ of Formula I is $CH_3$.

It is believed that in order to obtain selective attachment of the phosphatrane at the nitrogen center to obtain an anion exchange membrane having primarily groups of Formula II, the $R^1$ group attached to the phosphorus atom in the phosphatrane starting material is a $C_{1-5}$ alkyl group, a benzyl group or a halogen, and at least one of the equatorial nitrogen atoms is attached to a hydrogen atom. Such a configuration makes it less likely that the sulfonyl group of the sulfonated fluoropolymer support will attach at the phosphorus atom (yielding a group of Formula I) and more likely that a group of Formula II will be obtained.

Therefore, in order to increase selectivity for groups of Formula II, phosphatrane cation precursors wherein $R^1$ is $CH_3$ [in which there is no transannular bond (Laramay, M. A., Verkade, J. G., Zeitschr. fuer Anorg and Allgem. Chem., 1991, 605, 163-74)] or a halogen, such as fluorine or chlorine [in which each have a transannular bond], $R^2$ is H, and $R^3$ is a methyl group $CH_3$, or larger alkyl group, may be used in synthesis of the anion exchange membrane. The presence of an exocyclic halide group or alkyl chain at the phosphorous center prevents the reaction of the sulfonyl group with the phosphorous center, thus exclusively creating groups of Formula II through the reaction of the sulfonyl group with one of the equatorial NH groups of the phosphatranium salt. A variety of phosphatrane cations possessing exocyclic phosphorous substituents other than H have been reported in the literature. For example, cations of the type [X—P(MeNCH$_2$CH$_2$)$_3$N]$^+$ have been reported where X is (MeS)(S=)C— or (MeS)PhN=)C— (Tang, J. S., et al., J. Am. Chem. Soc., 1992, 114, 3129-3131; Xi, S. K., et al., Inorg. Chem., 1990, 29, 2214-2220); Cl, Ph$_2$(O)PO— (Liu, X., et. al., Inorg. Chem., 1998, 37, 5189-5197); F—, Cl—(Kingston, J. V., et al., Abstracts of Papers, 231$^{st}$ ACS Nat'l Meeting, Atlanta, Ga., Mar. 26-30, 2006, INOR-717); H$_2$N— (Liu, X., et al., Inorg. Chem., 2004, 43, 7431-7440); and, NC— or CN— (Kingston, J. V., et al., Angew. Chem. Intl. Ed., 2005, 44, 4960-4963), all of which are incorporated by reference herein.

In addition, one or more embodiments include an anion exchange membrane comprising a sulfonated fluoropolymer support to which only groups of Formula I or II are covalently bonded to one or more sulfonyl groups of the fluoropolymer support.

IV. Specific Sulfonated Fluoropolymer Support

In additional embodiments, the anion exchange membrane of the present invention comprises groups of Formula (I) and/or Formula (II) covalently bonded to a sulfonated fluoropolymer support comprising one or more groups of formula (III):

—(CF$_2$CF$_2$)$_x$—(CFRCF$_2$)—       (III)

wherein x is an integer greater than 1;

wherein R is (O—CF$_2$CF)$_z$ CF$_3$—O—CF$_2$CF$_2$—SO$_2$R$^1$, wherein z is an integer greater than 1 and wherein $R^1$ is a group of Formula I or Formula II.

An exemplary sulfonated fluoropolymer support compatible with one or more of the embodiments of the present invention is Nafion®, having the following general structure of Formula IV:

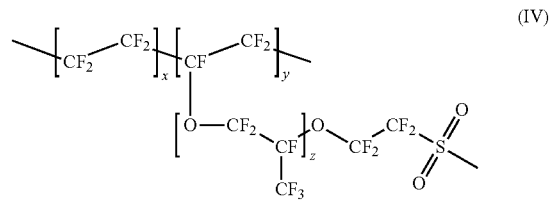

(IV)

A sulfonated fluoropolymer, such as the above, may be prepared by methods known in the art or can be purchased from any number of existing manufacturers. The manner in which the sulfonated fluoropolymer is produced is not within the scope of the present invention.

Preferably, x is an integer greater than 1, y is 1, and z is an integer between 1 and 2.

One aspect of one or more embodiments of the present invention is that the resonance delocalization of the positive charge on the bicyclic proazaphosphatrane cation and the tricyclic azaphosphatrane cation of the membrane effectively inhibits anions from forming interactive ion pairs with the cation, thereby maximizing anion mobility across the membrane. Another aspect of the one or more embodiments is that the bonds in the cage-like structures of proazaphosphatranes and azaphosphatranes are quite unstrained, thereby contributing to the stability of these systems. Another aspect of the one or more embodiments is that the cage-like structures of proazaphosphatranes and azaphosphatranes are quite compact, thereby offering protection of the carbon and phosphorus atoms they contain from nucleophilic attack and consequent ring opening reactions. Another aspect of the one or more embodiments is that the P—S bonds in the cage-like structures of proazaphosphatranes are known to be quite strong. As a consequence of the aforementioned properties, another aspect of the one or more embodiments is that the membrane can survive harsh and strongly basic conditions at elevated temperatures for an extended period of time. For example, as discussed in more detail below, one embodiment of the present invention was conductive at temperatures of 25° C. and in alkaline environments having pH greater than 14 (50% NaOH) for approximately 24 hours per run.

V. Anion Exchange Membrane Synthesis

One embodiment of the process of preparing an anion exchange membrane of the one or more embodiments of the present invention is straightforward. In the first step, excess phosphatranium salt and an organic solvent are added to a microwave vial containing a solid sulfonated fluoropolymer support such that the membrane is completely immersed in the solution of solvent and phosphatrane salt. The vial is subsequently treated in order to covalently bond the phosphatrane functionalities to the sulfonyl groups of the sulfonated fluoropolymer support. Next, the support can be washed with a polar, reasonably volatile solvent to remove the phosphatrane salt and organic solvent. Finally, the support can be soaked in an aqueous salt or hydroxide solution and subsequently dried.

Various phosphatrane salts may be prepared in the laboratory, as described herein and the references cited herein, or purchased from a number of manufacturers, including but not limited to phosphatrane chloride, phosphatrane bromide and phosphatrane iodide. However, any anion may used to form the phosphatrane salt in place of the halides described herein. The phosphatrane salt should be added in excess so as to increase the loading of the phosphatrane functionalities.

The organic solvent subsequently added to the sulfonated fluoropolymer support and phosphatrane salt can be any polar solvent. Exemplary solvents include but are not limited to dimethylformamide (DMF), dimethyl sulfoxide (DMSO) and ketones with high boiling points, such as acetone, butanone, isophorone or acetophenone. The advantage to using DMSO or a high-boiling ketone as the solvent is that no amine functionalities will be present in the solution, thus limiting any impurities that may form on the anion exchange membrane. Sufficient solvent should be added so that the sulfonated fluoropolymer support is immersed in the solution.

After the solution and support are prepared as described above, the phosphatrane ions are bonded to the sulfonyl groups of the sulfonated fluoropolymer support. This can be done by any number of methods known to one of skill in the art, including but not limited to heating the support in the presence of the corresponding salt thermally or via microwaving or radiation grafting under conditions that do not degrade the sulfonated fluoropolymer support and that encourage bonding between the sulfonyl groups and phosphatrane ions.

Subsequent to bonding the phosphatrane cations to the sulfonated fluoropolymer support, the support is rinsed with a polar solvent in order to remove any unreacted phosphatranium salt and solvent. Possible solvents include but are not limited to a lower alcohol, acetone or tetrahydrofuran (THF). Methanol is a preferred solvent because it is less likely to precipitate the soaking salt or hydroxide and, thus, contaminate the membrane.

Prior to use as an anion exchange membrane, the support is soaked in a hydroxide or aqueous salt solution. The purpose of soaking the support is to exchange the halide ions present in the support for hydroxide ions. Any strongly basic solution having the formula MOH, where M is a Group 1 metal, or $M(OH)_2$, where M is any Group 2 metal except Be, is preferable for soaking the support.

Standard methods known to one of ordinary skill in the art may be used to further dry the anion exchange membrane before use. For example, applying increased temperatures under reduced pressure, otherwise evaporating the excess liquid from the membrane, or exposing the membrane to a gentle stream of air or nitrogen will be sufficient to dry the membrane.

Other methods of bonding a phosphatrane to a sulfonated fluoropolymer support known to one of ordinary skill in the art may be used to obtain the one or more embodiments of the present invention, including but not limited to radiation grafting.

The thickness of the one or more embodiments of the present anion exchange membrane will be limited to the extent that it will be no thinner than the starting sulfonated fluoropolymer support.

VI. Use of Anion Exchange Membrane in a Fuel Cell

The compounds of the present invention, once prepared, are highly useful in a variety of applications, most preferably as an anion exchange membrane in a fuel cell. With reference to FIG. 1, one or more embodiments of the anion exchange membrane 1 of the present invention may be placed between an anode 2 and cathode 3 in a fuel cell. Methanol fuel is fed to the anode 2, while water and oxygen are fed to the cathode 3 side of the fuel cell. At the anode 2, methanol reacts with hydroxide ions to produce carbon dioxide, water and electrons. The electrons are transported through an external circuit 4 to provide electricity and back to the cathode 3. At the cathode 3, the electrons interact with oxygen and water to produce hydroxide ions, which are transported from the cathode 3 across the anion exchange membrane 1 to the anode 2 where oxidation of methanol occurs.

The one or more embodiments of the fuel cell assembly are usually operated at a temperature of at least 0° C., preferably at least 20° C., more preferably at least 50° C., The maximum temperature during operation is usually 150° C., more preferably 100° C., and most preferably 80° C.

The unique structure of the proazaphosphatrane and azaphosphatrane cations bound to the sulfonated fluoropolymer support in the various embodiments of the anion exchange membrane of the present invention facilitate the transport of hydroxide ions across the AEM by minimizing cation-anion interactions—a result of the distribution of the positive charge over the structures of the phosphatranium ions, as discussed above and exhibited in the various resonance structures of the proazaphosphatranium and azaphosphatranium cations. In addition, the cage-like structures adds the stability necessary to operate in strongly basic conditions at elevated temperatures.

More specifically, preparation of one or more embodiments of the present invention can be described by reference to following example.

Example 1

As illustrated in Scheme 1, a Nafion-F® membrane (6 cm×6 cm), with a 0.9 mmol/g loading of $SO_2F$ functionality and a thickness of 25 μm (DuPont, obtained from Ion Power Sources, Inc.) was charged to a microwave vial. To this was added excess phosphatranium chloride (500 mg, 2.3 mmol) and dry dimethylformamide (approximately 8 mL) (DMF) in order to immerse the membrane in solution. The membrane was then microwaved at 180° C. for 5 hours using a 300 W CEM Discover apparatus. The membrane was then washed with copious amounts of methanol to remove any unreacted phosphatranium salt, HX, and DMF. For electrical measurements, the Naf-Phan-X membrane was soaked in aqueous NaOH to exchange the halide ions for hydroxide, giving Naf-Phan-OH.

Electrical measurements were carried out on the anion exchange membrane prepared in Example 1. Table 1 details the results of the resistance and conductivity measurements for the anion exchange membrane prepared in Example 1. Resistance and conductivity measurements were conducted using the membrane prepared in Example 1 at 25° C. after washing with deionized water and/or a hydroxide solution of varying concentrations, as described in Table 1. Hydroxide conduction was tested in a methanol-based fuel cell. Due to the elevated temperature at which the membrane is prepared, 180° C., it is expected that it will operate and not degrade or lose performance in temperatures up to at least 150° C.

SCHEME 1

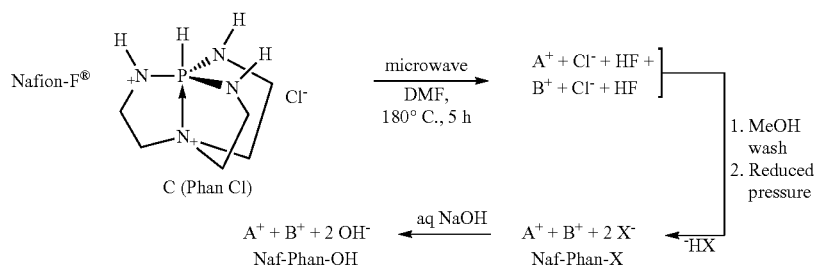

where A+ and B+ are:

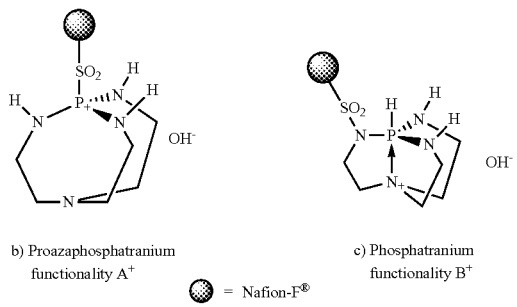

b) Proazaphosphatranium functionality $A^+$ c) Phosphatranium functionality $B^+$ ⬤ = Nafion-F®

The above process produced an anion exchange membrane having the following structure as described in X. Kong, et. al., *Macromolecules*, 2009, 42, 1659-1664:

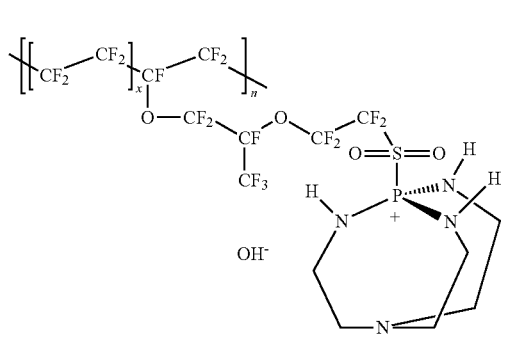

TABLE 1

| Wash Solution | Resistance (Ohms) | | | | Avg resistance (Ohms) | Conductivity (S/cm) |
|---|---|---|---|---|---|---|
| DI/4MNaOH | 0.345 | 0.347 | 0.349 | 0.351 | 0.348 | 0.00109 |
|  | 0.350 | 0.346 | 0.035 |  |  |  |
| 4MNaOH(1) | 0.468 | 0.469 | 0.454 |  | 0.459 | 0.00083 |
|  | 0.453 | 0.451 |  |  |  |  |
| DI/1MNaOH(1) | 0.340 | 0.340 | 0.338 |  | 0.339 | 0.00112 |
| 4MNaOH(2) | 0.323 | 0.324 | 0.324 |  | 0.324 | 0.00117 |
| 50% NaOH | 0.380 | 0.410 | 0.425 | 0.436 | 0.427 | 0.00089 |
|  | 0.449 | 0.459 |  |  |  |  |
| 4MNaOH(3) | 0.435 | 0.428 | 0.430 | 0.437 | 0.433 | 0.00088 |
| 1MNaOH(2) | 0.410 | 0.377 | 0.376 | 0.370 | 0.383 | 0.00099 |
| DI/1MNaOH(3) | 0.292 | 0.291 | 0.289 | 0.291 |  | 0.00130 |
| DI | 0.320 | 0.325 |  |  | 0.323 | 0.00117 |

Figure 2:
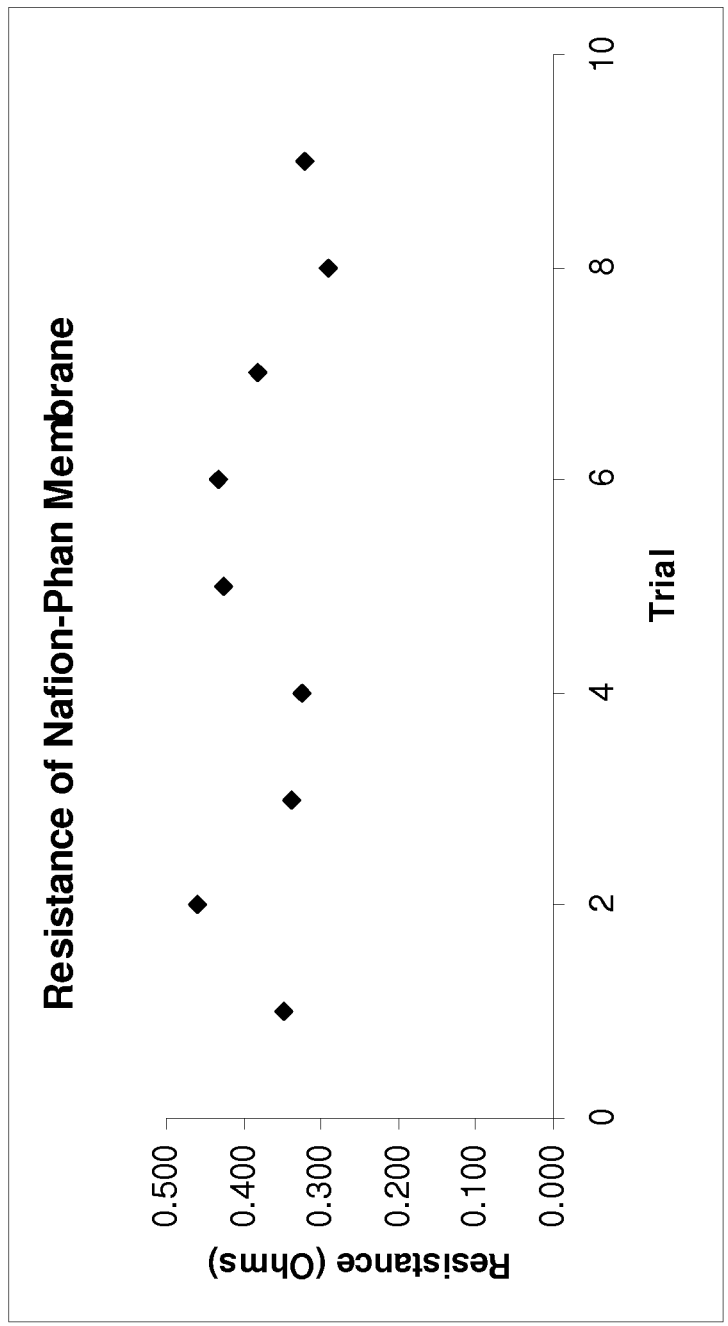
FIG. 2 is a resistance plot of the performance of one embodiment of the present invention under operating conditions.

FIG. 2 is a resistance plot demonstrating the average figures from Table 1 for the nine solutions. As can be seen from Table 1 and FIG. 2, the anion exchange membrane of Example 1 exhibited low resistance in the presence of hydroxide ions, while maintaining its conductivity, in highly basic conditions. Visual observation of the membrane revealed that the membrane remained in good mechanical condition after repeated exposure to highly alkaline environments.

While prior anion exchange membranes have provided adequate conductivity at ambient temperatures and relative humidity of 100%, they have degraded upon subsequent amination and hydroxide ion exchange and was not evaluated in highly alkaline environments present in a fuel cell in which the membrane would be used. (Danks, T. N., et al., *J. Mater. Chem.*, 2002, 12, 3371).

Example 2

As discussed above, this method should also be useful in providing anion exchange membranes having a variety of $R^1$-$R^5$ groups attached to the corresponding proazaphosphatrane or azaphosphatrane covalently bonded to the sulfonated fluoropolymer support.

For example, in order to obtain an anion exchange membrane having groups of Formula I wherein $R^1$, $R^2$, and $R^3$=$CH_3$ and $R^4$ and $R^5$=H a process similar to that described above may be used. First, the sulfonated fluoropolymer support is placed in a microwave vial. Excess phosphatranium chloride salt and an organic solvent, such as DMF, are added to the vial containing the sulfonated fluoropolymer support in amounts similar to that described above in Example 1. Such a phosphatrane compound is obtainable by methods known in the art, including but not limited to those described in Lensink, C., et al., J. Am. Chem. Soc. 1989, 111, 3478-3479, and Laramay, M. A. and Verkade, J. G., Z. Anorg. Allg. Chem, 605 (1991), 163-174. For example, a solution of $(HMeNCH_2CH_2)_3N$ in $CH_2Cl_2$ is added to a solution of CIP $(NMe_2)_2$ in $CH_2Cl_2$. The solution is stirred and the solvent is removed, thus resulting in the phosphatrane salt $HP(CH_3NCH_2CH_2)_3N^+$ $Cl^-$. The salt and an organic solvent are added to the vial containing the sulfonated fluoropolymer support and placed in a microwave at a temperature and for a time sufficient to covalently bond the phosphatrane to the sulfonyl groups of the fluoropolymer support. The membrane is then washed with copious amounts of methanol to remove any unreacted phosphatranium salt, HX, and DMF.

Example 3

In order to obtain an anion exchange membrane having groups of Formula I wherein $R^1$, $R^2$, and $R^3$ are a benzyl group (i.e., $CH_2C_6H_5$), a process similar to that described above may be used. First, the sulfonated fluoropolymer support is placed in a microwave vial. Excess phosphatranium chloride and organic solvent, such as DMF, are added to the vial containing the sulfonated fluoropolymer support in amounts similar to that described above in Example 1. Such a phosphatrane compound is obtainable by methods known in the art, including but not limited to those described in Lensink, C., et al., J. Am. Chem. Soc. 1989, 111, 3478-3479, and Laramay, M. A. and Verkade, J. G., Z. Anorg. Allg. Chem., 605 (1991), 163-174. For example, a solution of $PCl_3$ in $CH_2Cl_2$ is added to a solution containing $P(NMe_2)_3$ in $CH_2Cl_2$. To this solution is added a solution of tris-(N-benzyl-2-aminoethyl)amine in $CH_2Cl_2$. The solution is stirred and the solvents are removed, thus resulting in the salt $HP((PhCH_2)NCH_2CH_2)_3N^+$ $Cl^-$. The salt and an organic solvent are added to the vial containing the sulfonated fluoropolymer support and placed in a microwave at a temperature and for a time sufficient to covalently bond the phosphatrane to the sulfonyl groups of the fluoropolymer support. The membrane is then washed with copious amounts of methanol to remove any unreacted phosphatranium salt, HX, and DMF.

Example 4

In order to obtain an anion exchange membrane having primarily groups of Formula II, wherein at least one of $R^1$, $R^2$ or $R^3$ is H, and the other two R groups are any $C_{1-5}$ alkyl or halide group, and $R^4$ and $R^5$ are H, a process similar to that described above may be used. First, the sulfonated fluoropolymer is placed in a microwave vial. Excess amounts of an appropriate phosphatranium chloride salt and an organic solvent, such as DMF, are added to the vial containing the sulfonated fluoropolymer support in amounts similar to that described above in Example 1. Such a phosphatrane compound is obtainable by methods known in the art, including but not limited to those described in Lensink, C., et al., J. Am. Chem. Soc., 1989, 111, 3478-3479, and Laramay, M. A. and Verkade, J. G., Z. Anorg. Allg. Chem., 1991, 605, 163-174. For example, a solution of $(HRNCH_2CH_2)_2(N(CH_2CH_2NH_2)$ (R=e.g., i-Pr) in $CH_2Cl_2$ is added to a solution of CIP $(NMe_2)_2$. The solution is stirred and the solvent is removed, thus resulting in the salt. The resulting salt is deprotonated to obtain the corresponding free proazaphosphatrane. The free proazaphosphatrane can then be decorated with a variety of groups at the phosphorus center, such as halides (F, Cl, Br or I) or alkyl chains, to obtain the corresponding quaternary salts. This can be achieved through reacting a proazaphosphatrane with a source of $X_2$, where X=F, Cl, Br or I. (Kingston, J. V., et al., *J. Organ. Chem.*, 2007, 72(8), 2816-2822; Laramay, M. A. and Verkade, J. G., Z. Anorg. Allg. Chem., 1991, 605, 163-174).

The quaternary salt and organic solvent are added to the vial containing the sulfonated fluoropolymer support and placed in a microwave at a temperature and for a time sufficient to covalently bond the phosphatrane to the sulfonyl groups of the fluoropolymer support. The membrane is then washed with copious amounts of methanol to remove any unreacted phosphatranium salt, HX, and organic solvent. As a result, an anion exchange membrane having azaphosphatrane cations of Formula II where $R^1$ is H, $R^2$ is X (where X=Cl, F, Br or I), $R^3$ is i-Pr, and $R^4$ and $R^5$ are H is obtained.

It is to be understood that the above-described arrangements are only illustrative of the application of the principles of the present invention and it is not intended to be exhaustive or limit the invention to the precise form disclosed. Numerous modifications and alternative arrangements may be devised by those skilled in the art in light of the above teachings without departing from the spirit and scope of the present invention. For example, the R1-5 groups may be groups other than those specifically enumerated herein and in the claims without varying the spirit and purpose of the invention, which is the use of a phosphatrane cation with varying side chains on a sulfonated fluoropolymer support that is relatively simple to fabricate. It is intended that the scope of the invention be defined by the claims appended hereto.

In addition, the previously described versions of the present invention have many advantages, including but not limited to those described above. However, the invention does not require that all advantages and aspects be incorporated into every embodiment of the present invention.

All publications and patent documents cited in this application are incorporated by reference in their entirety for all purposes to the same extent as if each individual publication or patent document were so individually denoted.

We claim:

1. An anion exchange membrane for use in a direct methanol fuel cell comprising a sulfonated fluoropolymer support covalently bonded to one or more phosphatrane cations.

2. The anion exchange membrane of claim 1, wherein the phosphatrane cation is a bicyclic proazaphosphatrane cation and wherein the sulfonated fluoropolymer support is covalently bonded to the phosphorous atom of the one or more proazaphosphatrane cations.

3. The anion exchange membrane of claim 2, wherein the one or more bicyclic proazaphosphatrane cations have the structure of formula (I)

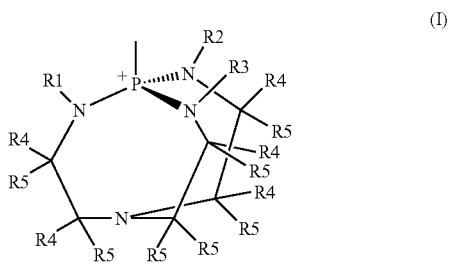

(I)

are covalently bonded to one or more sulfonyl groups of the sulfonated fluoropolymer support, wherein $R^1$, $R^2$ and $R^3$ are independently H, a $C_{1-5}$ alkyl group, a benzyl group, $C_{5-9}$ aryl group, $C_{1-4}$alkyl-$C_{6-9}$aryl, $((C_{1-4})$alkyl$)_3$Si, CH(Me)(Ph), Si(CH$_3$)$_3$, or 2,2-dimethylpropyl;

wherein $R^4$ and $R^5$ are independently H, a $C_{1-5}$ alkyl group, a $C_{5-9}$ aryl group, or a benzyl group; and, wherein a positive charge resides at the phosphorus atom or at any of the three equatorial nitrogen atoms bonded to the phosphorus atom.

4. The anion exchange membrane of claim 3, wherein $R^1$, $R^2$, $R^3$, $R^4$ and $R^5$ are H.

5. The anion exchange membrane of claim 3, wherein $R^1$ is H, $R^2$ and $R^3$ are CH$_3$ and $R^4$ and $R^5$ are H.

6. The anion exchange membrane of claim 3, wherein $R^1$, $R^2$ and $R^3$ are methyl groups, and $R^4$ and $R^5$ are H.

7. The anion exchange membrane of claim 3, wherein $R^1$, $R^2$ and $R^3$ are benzyl groups, and $R^4$ and $R^5$ are H.

8. The anion exchange membrane of claim 3, wherein $R^4$ and $R^5$ are independently $C_{1-5}$ alkyl groups.

9. The anion exchange membrane of claim 3, wherein at least one of $R^1$, $R^2$, $R^3$, $R^4$ and $R^5$ is H.

10. The anion exchange membrane of claim 3, wherein at least one of $R^1$, $R^2$, $R^3$, $R^4$ and $R^5$ is CH$_3$.

11. The anion exchange membrane of claim 3, wherein the sulfonated fluoropolymer support comprises groups of formula (IV)

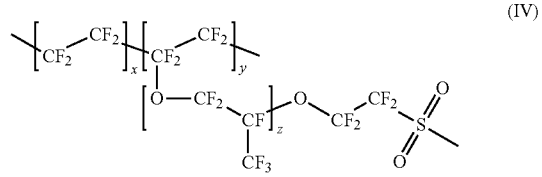

(IV)

wherein x is an integer greater than 1;
wherein y is 1; and,
wherein z is an integer between 1 and 2.

12. The anion exchange membrane of claim 3, wherein the sulfonated fluoropolymer support is Nafion®.

13. The anion exchange membrane of claim 2, further comprising one or more tricyclic azaphosphatrane cations covalently bonded to one or more sulfonyl groups of the sulfonated fluoropolymer support, wherein the sulfonyl group is bonded to any one of the three equatorial nitrogen atoms of the azaphosphatrane cation.

14. The anion exchange membrane of claim 13, wherein one or more tricyclic phosphatrane cations having the structure of formula (II)

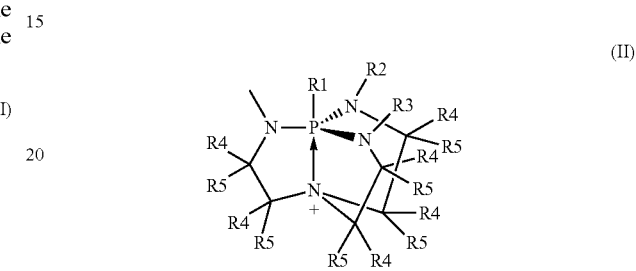

(II)

are covalently bonded to a sulfonyl group of the sulfonated fluoropolymer support, wherein $R^1$ is H, a $C_{1-5}$alkyl group, a benzyl group or a halogen;

wherein $R^2$ and $R^3$ independently are H, a $C_{1-5}$ alkyl group, a benzyl group, $C_{5-9}$ aryl group, $C_{1-4}$alkyl$C_{6-9}$aryl, $((C_{1-4})$alkyl$)_3$Si, CH(Me)(Ph), Si(CH$_3$)$_3$, or 2,2-dimethylpropyl;

wherein at least one of $R_1$, $R_2$ and $R_3$ is H; and, wherein $R^4$ and $R^5$ independently are H, a $C_{1-5}$ alkyl group, a $C_{5-8}$ aryl group, or a benzyl group; and, wherein a positive charge resides at the basal nitrogen atom.

15. The anion exchange membrane of claim 14, wherein $R^1$, $R^2$, $R^3$, $R^4$ and $R^5$ are H.

16. The anion exchange membrane of claim 14, wherein $R^1$ is F or Cl and $R^2$, $R^3$, $R^4$ and $R^5$ are H.

17. The anion exchange membrane of claim 14, wherein $R^1$ is CH$_3$ and $R_2$, $R_3$, $R_4$ and $R_5$ are H.

18. The anion exchange membrane of claim 14, wherein $R^1$ is F or Cl, $R^2$ is H, $R^3$ is a methyl or benzyl group, and $R^4$ and $R^5$ are H.

19. The anion exchange membrane of claim 14, wherein at least one of $R^1$, $R^2$, $R^3$, $R^4$ and $R^5$ is H.

20. The anion exchange membrane of claim 14, wherein at least one of $R^1$, $R^2$, $R^3$, $R^4$ and $R^5$ is CH$_3$.

21. The anion exchange membrane of claim 1, wherein the phosphatrane cation is a tricyclic azaphosphatrane cation and wherein one or more sulfonyl groups of the sulfonated fluoropolymer support is covalently bonded to an equatorial nitrogen atom of the one or more azaphosphatrane cations.

22. The anion exchange membrane of claim 21, wherein the one or more tricyclic azaphosphatrane cations have the structure of formula (II)

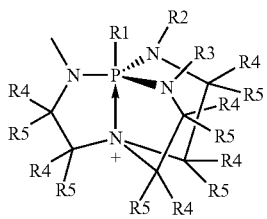 (II)

are covalently bonded to a sulfonyl group of the fluoropolymer support, wherein $R^1$ is H, a $C_{1-5}$ alkyl group, a benzyl group or a halogen;

wherein $R^2$ and $R^3$ independently are H, a $C_{1-5}$ alkyl group, a benzyl group, $C_{5-9}$ aryl group, $C_{1-4}$alkyl$C_{6-9}$aryl, $((C_{1-4})$alkyl$)_3$Si, CH(Me)(Ph), Si(CH$_3$)$_3$, or 2,2-dimethylpropyl;

wherein $R^4$ and $R^5$ independently are H, a $C_{1-5}$ alkyl group, a $C_{5-8}$ aryl group, or a benzyl group; and, wherein a positive charge resides at the basal nitrogen atom.

23. The anion exchange membrane of claim 22, wherein $R^1$, $R^2$, $R^3$, $R^4$ and $R^5$ are H.

24. The anion exchange membrane of claim 22, wherein $R^1$ is F or Cl and $R_2$, $R_3$, $R_4$ and $R_5$ are H.

25. The anion exchange membrane of claim 22, wherein $R^1$ is CH$_3$ and $R^2$, $R^3$, $R^4$ and $R^5$ are H.

26. The anion exchange membrane of claim 22, wherein $R^1$ is F or Cl, $R^2$ is H, $R^3$ is a methyl or benzyl group, and, $R^4$ and $R^5$ are H.

27. The anion exchange membrane of claim 22, wherein at least one of $R^1$, $R^2$, $R^3$, $R^4$ and $R^5$ is H.

28. The anion exchange membrane of claim 22, wherein at least one of $R^1$, $R^2$, $R^3$, $R^4$ and $R^5$ is CH$_3$.

29. The anion exchange membrane of claim 22, wherein $R^1$ and $R^2$ are independently a $C_{1-5}$ alkyl group or halogen, and $R^3$, $R^4$ and $R^5$ are H.

30. A direct methanol fuel cell comprising the anion exchange membrane claim 1.

* * * * *